United States Patent

Andersson et al.

[11] Patent Number: 4,530,662
[45] Date of Patent: Jul. 23, 1985

[54] IMPRESSION TRAY FOR DENTAL PURPOSES

[76] Inventors: Bror A. E. Andersson, Österängsvägen 24, S-182 46 Enebyberg; Ragnvald E. Lindblom, Alsäter, S-740 10 Almunge, both of Sweden

[21] Appl. No.: 488,643

[22] Filed: Apr. 26, 1983

[51] Int. Cl.³ ............................................. A61C 9/00
[52] U.S. Cl. ............................................................ 433/37
[58] Field of Search ................................... 433/37, 38

[56] References Cited

U.S. PATENT DOCUMENTS 3,534,475  10/1970  Hilaire .................................... 433/37

FOREIGN PATENT DOCUMENTS 415264  8/1934  United Kingdom ................... 433/37
460817  2/1937  United Kingdom ................... 433/37

Primary Examiner—Robert Peshock
Attorney, Agent, or Firm—Young & Thompson

[57] ABSTRACT

An impression tray for dental purposes has a shovel-like blade provided on its inside with layer forming attachments for a semi-liquid or plastic impression material which is put onto the tray when it is pressed against the lower or upper jaw for taking an impression. The layer is of uniformly distributed threads with closely-lying attachment points on the inside of the tray, the threads having a stiffness such that they can penetrate into the semi-liquid or plastic impression material when the tray with the material is pressed against the respective jaw for the purpose of the layer being incorporated as effective anchoring means in the bottom layer of the impression material when the material has solidified and the tray is to be jerked loose. The threads are in the form of a non-woven fabric and are bonded to each other at their contact points.

7 Claims, 11 Drawing Figures

IMPRESSION TRAY FOR DENTAL PURPOSES

The present invention relates to an impression tray for dental purposes and is of the kind consisting of a shovel-like blade with a fixed or a removable handle, the blade being provided, at least at certain portions of its inside, with means forming attachments for the impression material. The latter is usually an aliginate or consists of different types of rubber compositions, silicone compositions or combinations of silicone and alginate, which are initially plastic or semi-liquid.

When a dentist takes an impression of an entire upper or lower jaw or parts thereof, he uses different types of metal or plastics impression trays. The tray is filled with plastic or semi-liquid impression material and is then put in place in the mouth. When the impression material has solidified, the tray together with the elastic, solidified impression material is removed with a jerk from the jaw. Undercutting, e.g., between certain teeth, makes it necessary to use quite a large force when the tray is to be removed. To keep the impression material on the tray, those of the prior art have been provided i.a. with small holes. As the impression is being made, impression material is partially forced out through the holes and attaches the material to these points of the tray.

However, most known impression trays lack holes in the front portion, due to manufacturing difficulties. Instead, projections have been made on the inside for preventing the impression material from easing from the tray at these places. Perforated trays are often not used when rubber compositions or the like are used as impression material. Adhesion between tray and impression material is then usually provided by the tray being treated beforehand with an adherent which then adheres to the impression material. In this technique the tray will be relatively difficult to clean after use, if the tray is going to be used several times.

When the tray and impression material are taken out from the mouth, the attachment between tray and impression material is subjected to very large stress. If the solidified impression material in the tray has eased away from the tray in some place during taking the impression, there will be an error in the model which is produced from the impression, and consequently on the finished crown, bridge or prosthetic work.

The impression material of today is practically perfect in exactitude, but the adhesion i.e. retention between tray and impression material is not satisfactory with the trays available on the market. The holes in the trays are very often quite insufficient for fastening the impression material to the tray when taking the impression, and furthermore, trays with holes are difficult to clean. The use of adhesive on the tray to attach the impression material does not function satisfactorily either. The adhesive is difficult to apply to the tray and difficult to remove by scraping after use and also results in time-consuming work.

With the trays of the prior art it thus often occurs that the impression material loosens from the tray due to the fastening being insufficient, which in turn causes great inconvenience since the impression must be taken once again.

If the impression material loosens at a place which cannot be inspected, e.g. if such loosening has taken place at a distance from the edges of the tray, i.e. under the material itself, the result can be that a bridge is made up on a model which has an error due to the impression itself having loosened without the dentist noticing this. The dentist will then have to alter large portions of his work either partially or completely, with large loss of time and inconvenience for the patient.

The object of the present invention is therefore to provide an impression tray of plastics for disposable use, the inside of the tray being provided with attachment means providing a secure fastening between the impression material and closely-lying spots on the inside of the tray. This is achieved with an impression tray which, in accordance with the invention, is distinguished in that the fastening means form a layer of uniformly distributed thread-shaped attachment means of such stiffness that they can penetrate into the bottom layer of the plastic or semi-liquid impression material and form anchoring means when the material is put onto the tray and pressed against the fastening means, which retain the material at spots lying close together on the inside of the tray after the material has solidified.

In a preferred embodiment of the invention the desired result is obtained with the aid of a thin layer of non-woven material having thin and long filaments. The filaments lie criss-cross and coact such that the tear strength of the material will be considerable, both in the longitudinal direction of the layer and in its transverse direction between the top and bottom sides of the layer. In relation to the thickness of the filaments the interstices between the filaments will usually be very large. Such a layer can easily be attached to the inside of the tray, e.g. with the aid of binding agent. Alternatively, the filament layer can be attached by pressing it directly onto the hot tray, e.g. during compression molding or vacuum molding.

After trying out the tray in the patient's mouth and possible corrections of its shape, the tray is ready to receive the impression material. When the tray is then pressed against the teeth, the impression material will be pressed with comparatively large force against the filament layer on the inside of the tray. The plastic or semi-liquid impression material thus penetrates down into the outer layer of the filament layer so that the filaments in it become effectively bedded into the impression material to form reinforcing in it, these filaments having a strong connection with the remainder of the filament layer and thereby with the filaments which are attached to closely-lying spots on the inside of the tray. Since the filament layer is suitably thin, in the order of magnitude of one or a few millimeters, the plastic or semi-liquid impression material can in most cases penetrate right down to the filaments lying in the vicinity of the inside of the tray or actually down to the inside of the tray. There is thus obtained a thin bottom layer of the impression material which is more or less in contact with the inside of the tray and reinforced with filaments which are securely attached thereto. After solidification of the impression material and thereby its reinforced bottom layer, the material will be essentially as effectively attached to the inside of the tray as with an effective adhesion of the material to the tray in a manner known per se. The advantage with this embodiment is, however, that in relation to the known adhesion there is avoided preparing the tray with adhesive before putting on the impression material, and furthermore the inventive tray can be used for different types of impression material independent of whether these function together with a given type of adhesive.

Since it is sought, with the tray in accordance with the invention, that the semi-liquid or plastic impression material shall penetrate down into the non-woven layer as far as possible and preferably right down to the inside of the tray, it is an advantage if the filament layer has a comparatively large resistance to compression so that the interstices between the filaments are kept open as far as possible during the pressure from the semi-liquid impression material. The possibilities for the impression material to be forced inbetween the filaments of the layer are thereby increased. A suitable non-woven layer for this purpose is a type of plastics filament layer used for certain known gas filters. The plastics filaments in these gas filters are disposed in all directions. The filament thickness is very small, e.g. of the order of magnitude 5 denier and the length thereof is very large. A great number of relatively large interstices are formed between the filaments. In order to maintain the size of the interstices as far as possible, the filaments are fixed to each other at their contact points. This can be achieved in different ways. One way is to use a binder. Another way is to fuse the filaments at their intersection points, the plastics filaments then being so-called by-component plastics filaments, where one component has a lower melting point than the other. Heating to the lower melting point results in fixation at the intersection points, while the component with the higher melting point will be unaffected and retains its fibrous form. A relatively stable three-dimensional network is formed in the different cases, which is extremely suitable as a fastener for the impression material in the tray in accordance with the invention.

The basic idea in the invention is thus that the filaments will form a reinforcement in the bottom layer of the impression material adjacently inside of the tray. However, the fastening can be further reinforced by the filaments being combined with some chemical agent known per se which binds the impression material. This chemical agent can in turn be added as an impregnation of the filaments or be applied to absorbing filaments which are mixed into the network of filaments forming the reinforcement itself.

Different types of fastening means arranged on the inside of an impression tray in accordance with the invention are illustrated as examples on the appended drawings.

Figure 5:
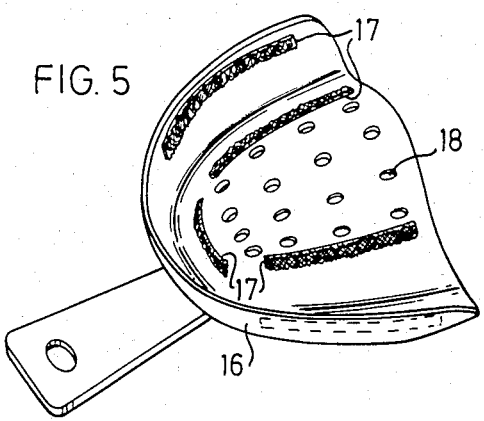
Figure 6:
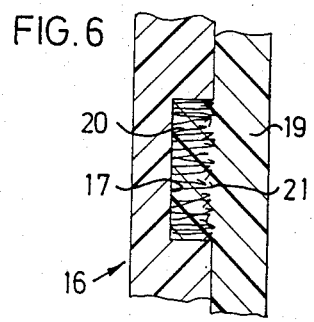
Figure 9:
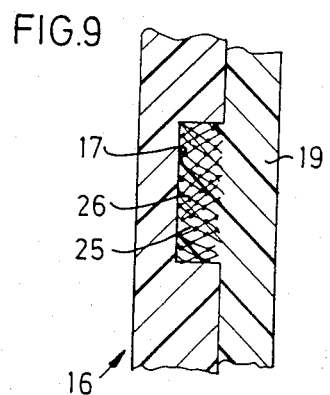
Figure 10:
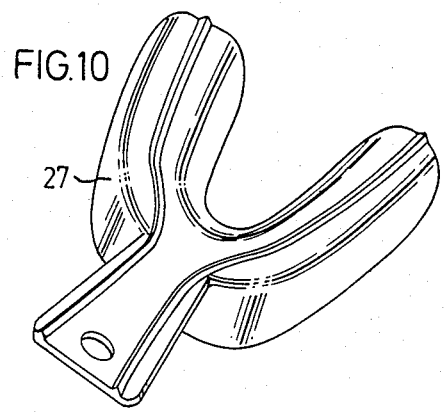
Figure 11:
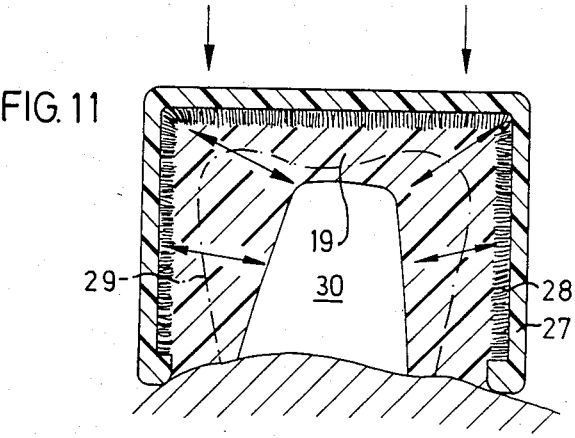

FIG. 5 is a schematic perspective view of a tray which is only provided at certain portions of its inside with fastening means according to the invention, which are disposed in depressions on the inside of the tray in this case, FIGS. 6 and 9 illustrate different embodiments of attachment means according to the invention, which, in the illustrated example are disposed in a depression in the tray according to FIG 5, FIG. 10 illustrates the tray in the form of a trough bent to a U-shape, and provided with reinforcement on the outside and with fastening means according to the invention on the inside, FIG. 11 is a cross-section through one of the legs of the U-shaped tray in FIG. 10 and schematically illustrates what forces occur.

As will be seen from FIGS. 1 to 4, the tray 10 is made from relatively thin plastics, since it is intended to be used only once. In the illustrated embodiment, the tray is provided with a mat or layer 11 of fastening means on its inside, the layer having a thickness suitably in the range of one to three millimeters. The fastening means comprises thin and long plastics filaments 12 which are mixed with each other to a non-woven layer in the illustrated example, and this layer can be easily fastened to the inside of the tray in different ways, as mentioned above. For these plastics filaments to have sufficient stiffness they are suitably attached to each other at the places 13 where they intersect and are in mutual contact. The felt or mat will thus be made up from a very large number of plastics filaments which have a length between their fastening points to adjacent filaments such that they form a three-dimensional network affording a certain amount of elastic resistance to compression. This type of felt or mat is known per se from certain types of filter cloths for filtering liquids or gases. By fastening such a filter cloth, known per se, on the inside of an impression tray there is obtained a layer of thread-shaped, relatively stiff attachment means having the ability to resist the pressure of the plastic or semi-liquid impression material when this is put onto the impression tray and pressed into engagement against the inside thereof. The material will then penetrate through the relatively thin layer of plastics filaments so that these become embedded in the material to form anchoring means when the material has solidified. The filaments are securely attached to each other and to the inside of the tray, thereby providing secure attachment of the solidified impression material at closely-lying points, since the filaments are incorporated as an effective reinforcing element in the bottom layer of the solidified impression material.

The thread-like attachment means according to the invention can, however, be disposed in limited areas of the inside of the tray, and can then be disposed to depressions in the tray, as is illustrated in FIG. 5 and the associated sections shown in FIGS. 6 to 9.

Figure 1:
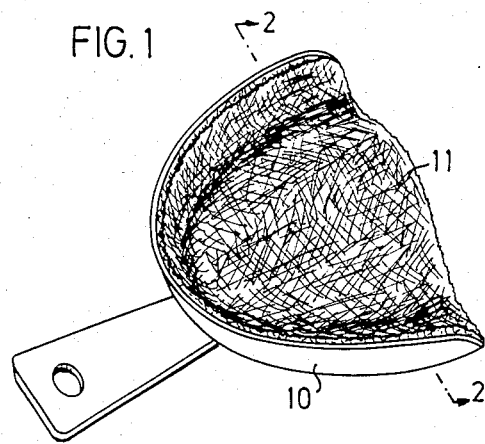
FIG. 1 is a schematic perspective view of a tray provided on its inside with a mat or a layer of attachment means in accordance with the invention.
Figure 2:
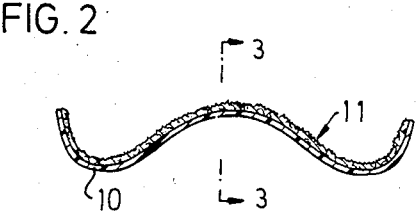
FIG. 2 is a cross-section along the line 2—2 in FIG. 1.
Figure 3:
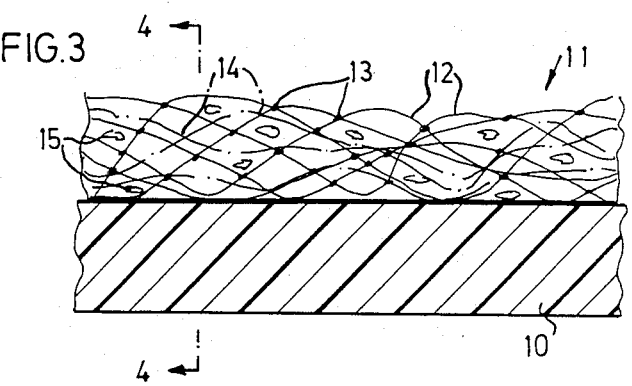
FIG. 3 is an enlarged partial depiction of the section in FIG. 2.
Figure 4:
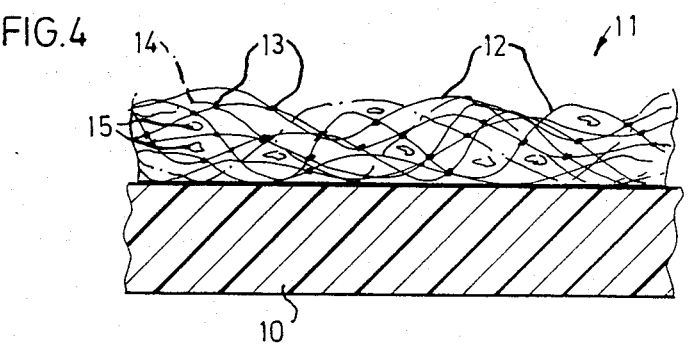
FIG. 4 is a section along the line 4—4 in FIG. 3.

In certain cases, the plastics filaments 12 in FIGS. 3 and 4 can be mixed with absorbing filaments 14 as indicated by chain-dotted lines. These absorbing filaments may comprise cellulose filaments and can be impregnated with a binder coacting chemically with the plastic or semi-liquid impression material being used and bind the filaments to it when the impression material solidifies. Alternatively, the layer 13 may be coated with a low-viscosity binder before putting on the impression material, the binder either binding the plastics filaments and/or the absorption filaments 14 to the impression material. Instead of the absorption filaments 14, or in combination with these, small absorption bodies 15, e.g. of cellulose particles, can be mixed into the layer 13 for filling the same function as the absorption filaments.

The described embodiment of FIGS. 1-4 is cheap in manufacture. The plastic tray 10 itself may be of a known embodiment, e.g. with a removable or attached handle. A non-woven layer 13 of the type described is attached to the tray. Since the tray is of relatively thin plastics, it is usual to manufacture it by compression moulding or vacuum moulding, whereby the plastics material is heated up and relatively soft. It is therefore simple to attach the fibrous filament layer in the form of a thin mat or felt which is pressed into the heated and soft plastics material of the tray so that the filaments are anchored in the plastics. Alternatively, the inside of the ready tray can be coated with a binder for gluing on the mat or felt of filaments.

It is essential in the different embodiments that the filaments are relatively dense so that they form closely-lying attachments points on the inside of the tray and that the filaments are forced to penetrate into the plastic or semi-liquid impression material to form the anchoring filaments in it. This reinforcement can be made still more secure with the aid of a binder, but normally this is not necessary to obtain satisfactory and secure attachment of the impression material.

The plastics tray 16 of FIG. 5 is provided with a plurality of depressions 17, of which one is illustrated in section in FIGS. 5-9 with different embodiments of the attachment means in accordance with the invention.

The tray is furthermore provided with holes 18, known per se, forming the attachment for the impression material 19. The depressions have suitably the same width in relation to each other, a strip of attachment means in accordance with the invention being fastened into the depressions with the aid of a binder.

In FIG. 6, the fastening means comprises plastics filaments 20 which are upstanding and attached at their feet to the tray 16. These filaments 20 are all of the same length, and at the outer ends they are formed with a hook 21 in the same way as for so-called teazel bands. The hooks 21 result in that the filaments will be securely anchored in the impression material 19.

Figure 7:
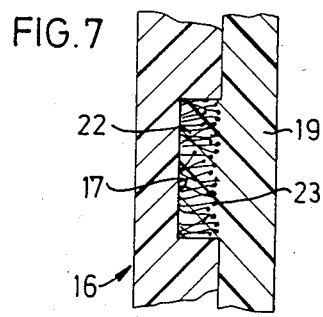

The plastics filaments 22 are arranged in the same way in FIG. 7 as in FIG. 6, but in this case their free end portions ar thicknened in relation to their inner end portions and provided with a nodule 23 resulting in that the filaments will be securely anchored in the impression material 19.

Figure 8:
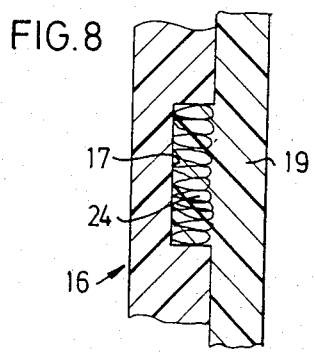

In FIG. 8 the filaments are formed into loops 24 forming anchoring means in the impression material 19.

FIG. 9 illustrates filaments 25 which cross each other to form a layer which is attached to the bottom of the depression 17 and to the inside on the tray 16. The filaments are firmly attached to each other at the intersection points 26, indicated by dots.

FIG. 10 illustrates a tray 27 with a wishbone-shape and a trough-shaped cross-section for the legs as illustrated in FIG. 11. The tray is clad on the inside with a layer 28 of fastening means according to the invention, said means penetrating into the impression material 19 to form an anchorage in it. A dotted line indicates a tooth 29 and a full line indicates the contour of a ground-off tooth 30 which is to be provided with a crown. The arrows in the figure indicate the forces occurring, which can be substantial when taking away the tray with the solidified impression material, thereby making great demands on a secure adhesion between the impression material and the inside of the tray.

We claim:

1. An impression tray for dental purposes, including a shovel-like blade which at certain portions of its inside is provided with means forming attachments for impression material which is put on the tray in a semi-liquid or plastic condition for taking an impression of a lower or upper jaw, the impression material being allowed to solidify before removing the tray, characterized by attachment means forming a layer of uniformly distributed thread-shaped attachment means, the thread-shaped attachment means having a stiffness such that they can penetrate into the semi-liquid or plastic impression material when the tray with the impression material is pressed against the respective jaw, such that the closely-lying attachment means will be incorporated as effective anchoring means in the bottom layer of the impression material when the impression material has solidified and the tray is to be removed, the attachment means forming a mat or felt of filaments in all directions to form a porous anchoring mat of filaments, said filaments being permanently secured to the tray wherever the filaments touch the tray, thereby to ensure removal of the tray and the filaments and the impression material as a unit.

2. Tray as claimed in claim 1, characterized in that the attachment means comprise fibrous elements which are very thin in relation to their length and which are incorporated in a non-woven layer the bottom side of which is attached to the inside of the tray.

3. Tray as claimed in claim 2, characterized in that the filament layer has a thickness of at most about 4 mm.

4. Tray as claimed in claim 3, characterized in that the filaments form an aery three-dimensional network by the filaments crossing each other in different directions and being mutually attached at the intersection points.

5. Tray as claimed in claim 3, characterized in that the filament layer has a thickness in the range of one to three millimeters.

6. Tray as claimed in claim 1, characterized in that the filaments are secured to the tray by a binding agent.

7. Tray as claimed in claim 1, characterized in that the filaments are secured to the tray by pressing directly onto the hot tray.

* * * * *